(12) United States Patent
Brown et al.

(10) Patent No.: US 9,220,817 B2
(45) Date of Patent: Dec. 29, 2015

(54) MEDICAL DEVICE

(71) Applicant: Stemnion, Inc., Pittsburgh, PA (US)

(72) Inventors: Larry R Brown, Newton, MA (US); George L Sing, New York, NY (US)

(73) Assignee: STEMNION, INC., Pittsburgh, PA (US)

( * ) Notice: Subject to any disclaimer, the term of this patent is extended or adjusted under 35 U.S.C. 154(b) by 0 days.

(21) Appl. No.: 14/204,073

(22) Filed: Mar. 11, 2014

(65) Prior Publication Data

US 2014/0271773 A1 Sep. 18, 2014

Related U.S. Application Data

(60) Provisional application No. 61/779,032, filed on Mar. 13, 2013.

(51) Int. Cl.
| | |
|---|---|
| *A61L 31/16* | (2006.01) |
| *A61L 27/14* | (2006.01) |
| *A61L 27/34* | (2006.01) |
| *A61L 27/54* | (2006.01) |
| *A61L 31/10* | (2006.01) |

(52) U.S. Cl.
CPC ............... *A61L 31/10* (2013.01); *A61L 27/34* (2013.01); *A61L 27/54* (2013.01); *A61L 31/16* (2013.01); *A61L 2300/414* (2013.01); *A61L 2300/426* (2013.01); *A61L 2300/606* (2013.01)

(58) Field of Classification Search
CPC ............. A61L 2300/252; A61L 2300/412; A61L 2300/414; A61K 38/1841; A61K 38/1858; A61K 38/1866; A61K 38/1891; A61K 35/50; A61K 35/12
See application file for complete search history.

(56) References Cited

U.S. PATENT DOCUMENTS

| | | | | |
|---|---|---|---|---|
| 5,585,267 | A * | 12/1996 | Jones et al. | ............... 435/402 |
| 8,088,732 | B2 | 1/2012 | Marshall et al. | |
| 2006/0165667 | A1 * | 7/2006 | Laughlin et al. | ........... 424/93.21 |
| 2006/0233766 | A1 * | 10/2006 | Messina et al. | .............. 424/93.7 |
| 2007/0077232 | A1 * | 4/2007 | Naughton et al. | ........... 424/93.2 |
| 2008/0020015 | A1 * | 1/2008 | Carpenter et al. | ............ 424/426 |

OTHER PUBLICATIONS

Kamiya et al. (2005, Experimental Eye Research 80: 671-679.*
Welt, F.G.P., et al., Arterioscler Thromb Vasc Biol 2002;22:1769-1776.
Bridges, A.W. and Garcia, A.J., J Diabetes Sci Technol 2008;2(6):984-994.
Berthal, N.M., et al., PLoS One, Sep. 2010, vol. 5, Issue 9, e12580.
Broggini, N., et al., J Dent Res 2006; 85(5):473-478.
Anderson, J.M., et al., Semin Immunol 2008; 20(2):86-100.

* cited by examiner

*Primary Examiner* — Daniel C Gamett
(74) *Attorney, Agent, or Firm* — Linda O. Palladino; Gail M. Kempler

(57) ABSTRACT

The invention is directed to an improved medical device. In particular, the invention is directed to an improved medical device having a coating comprising novel cellular factor-containing solution compositions (referred to herein as CFS compositions), such CFS compositions including conditioned medium compositions obtained from culturing extraembryonic cytokine secreting cells (ECS cells), including Amnion-derived Cellular Cytokine Solution (referred to herein as ACCS) obtained from culturing Amnion-derived Multipotent Progenitor (AMP) cells, dispersed in a polymeric coating material.

12 Claims, 1 Drawing Sheet

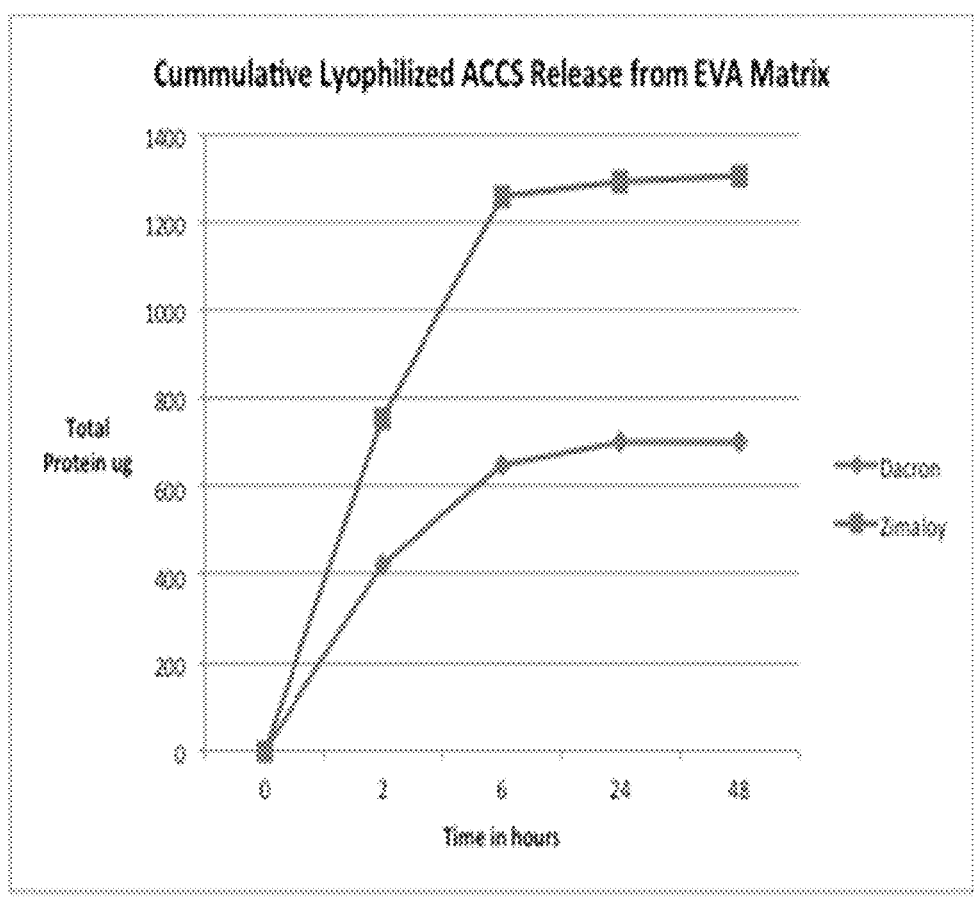

MEDICAL DEVICE

FIELD OF THE INVENTION

The field of the invention is directed to an improved medical device. In particular, the field of the invention is directed to an improved medical device having a coating comprising novel cellular factor-containing solution compositions (referred to herein as CFS compositions), such CFS compositions including conditioned medium compositions obtained from culturing extraembryonic cytokine secreting cells (ECS cells), including Amnion-derived Cellular Cytokine Solution (referred to herein as ACCS) obtained from culturing Amnion-derived Multipotent Progenitor (AMP) cells, dispersed in a polymeric coating material.

BACKGROUND OF THE INVENTION

There are approximately 25 million people in the U.S. with implanted, inserted or transcutaneous medical devices (see, for example, Hanna, K. E., Institute of Medicine (U.S.) Innovation and invention in medical devices: workshop summary. Washington, D.C: National Academy Press; 2001. Roundtable on Research and Development of Drugs B, and Medical Devices). The expected U.S. demand for such devices is increasing at 8% each year (see, for example, The Freedonia Group, Cleveland, Ohio, USA: Freedonia; 2010, Implantable Medical Devices to 2014—Demand and Sales Forecasts, Market Share, Market Size, Market Leaders). These devices include, but are not limited to, cardiac pacemakers, defibrillators, vascular grafts, dental implants, bone screws, catheters, coronary artery stents, staples, wires, shunts and joint replacement devices.

Although many medical devices perform adequately for years, implantation, insertion or transcutaneous placement of biomaterials and medical devices elicits a dynamic host inflammatory response (see, for example, Anderson, J. M., et al., Foreign body reaction to biomaterials, Semin Immunol 2008; 20(2):86-100, N. Broggini, L. M. McManus, J. S. Hermann, R. Medina, R. K. Schenk, D. Buser, and D. L. Cochran, Peri-implant inflammation defined by the implant-abutment interface, J Dent Res 85(5):473-478, 2006) that severely limits the integration and long-term performance of many medical devices, including joint prostheses, chemical biosensors, electrical leads/electrodes, therapeutic delivery systems, and tissue-engineered constructs, affecting millions of patients each year.

One important example with severe life threatening consequences is coronary stent implants. Coronary stents are frequently used subsequent to balloon angioplasty in order to maintain adequate coronary muscle blood flow. However the use of coronary stents fundamentally alters the vascular response to injury by causing an intense and prolonged inflammatory state (see, for example, Welt, F. and Rogers, C., Arterioscler Thromb Vasc Biol, 2002; 22: 1769-1776). This inflammatory condition causes smooth cell proliferation within the coronary artery walls as a result of damage and removal of the endothelial cell layer that lines the lumen of these vessels. Up to 60% of stent implantation results in restenosis.

A medical device that is improved such that the inflammatory response associated with its implantation, insertion or transcutaneous placement is prevented or down-regulated would have a huge impact on the success of implanted, inserted or transcutaneous devices (A W Bridges, and A J Garcia, Anti-Inflammatory Polymeric Coatings for Implantable Biomaterials and Devices, Journal of Diabetes Science and Technology, 2, (6):984-994, 2008). It is an object of the invention described below to provide such an improved medical device.

BRIEF SUMMARY OF THE INVENTION

Applicants present herewith for the first time the instant invention whose object is to employ the anti-inflammatory properties of CFS compositions, including Amnion-derived Cytokine Solution (ACCS), in order to prevent and/or down-regulate the inflammatory response associated with virtually all implanted, inserted or transcutaneously placed medical devices. It is also an object of the invention to deliver, in a controlled manner, physiologically relevant inflammatory response-modulating cytokines and growth factors that are capable of preventing and/or down-regulating the inflammatory response associated with virtually all implanted, inserted or transcutaneously placed medical device. It is also an object of the invention to deliver, in a controlled manner, physiologically relevant wound healing growth factors and cytokines that are capable of promoting healing of tissue at the medical device implantation, insertion or transcutaneous placement site in a patient.

Accordingly, it is an object of the instant invention to provide an improved medical device as well as methods for using the improved medical device, wherein the improved medical device has absorbed onto it novel cellular factor-containing solution compositions referred to herein as CFS compositions, including ACCS. The CFS compositions, including ACCS, contain a complex and unique combination of and physiologic levels of inflammatory response-modulating cytokines and growth factors found naturally in the body. The inflammatory response-modulating cytokines and growth factors contained in the CFS compositions, including ACCS, are released into the local area over time. Thus, the inflammatory response-modulating cytokines and growth factors are delivered precisely to the area for maximal effect. Because the inflammatory response-modulating cytokines and growth factors are present in levels comparable to physiological levels found in the body, they are optimal for use in therapeutic applications which require intervention to influence biochemical and biological processes such as the inflammatory response. The inflammatory response-modulating cytokines and growth factors are released slowly over time to provide a continual, consistent physiologic level of such inflammatory response-modulating cytokines and growth factors to prevent and/or down-regulate the inflammatory response associated with implanted, inserted, or transcutaneously placed medical devices as well as to optimize healing and/or recovery. In addition, CFS compositions, including ACCS, can be formulated prior to their absorption onto the medical device. Such formulations may include sustained-release/controlled-release/time-release/extended-release formulations or the addition of gelling or thickening agents to improve adsorption onto the medical device. Details on sustained-release formulations of CFS compositions, including ACCS, can be found in U.S. Pat. Nos. 8,058,066 and 8,088,732, both of which are incorporated herein by reference. Further, the CFS compositions, including ACCS, may be lyophilized prior to absorption onto the medical device. An important feature of the improved medical device described herein in that it is the first medical device disclosed that is capable of delivering numerous wound healing and inflammatory response-modulating cytokines and growth factors simultaneously, slowly and at physiologic concentrations directly to the site of implantation, insertion or transcutaneous placement of the medical device.

Tens of millions of medical devices are implanted, inserted or transcutaneous placed worldwide annually into patients for medical purposes. Unfortunately, any foreign material implanted into the body will result in an inflammatory reaction which will often result in encapsulation of the implanted, inserted or transcutaneously placed device. These biologic responses also result in decreasing the effectiveness of the medical devices and limiting their lifespan as useful prostheses, stents, etc. The sustained-release of CFS compositions, including ACCS, from coated medical devices would have a significant economic impact by increasing the effectiveness and biocompatibility as well as function of all medical device implants, insertions or transcutaneous placements and significantly reduce the number of failed devices.

Accordingly, a first aspect of the invention is an improved implantable medical device useful for surgical implantation into a subject's body, wherein the improvement to the implantable medical device comprises an implantable medical device having a coating on its surface, wherein the coating comprises Cellular Factor-containing Solution (CFS) compositions dispersed in a polymeric coating material.

A second aspect of the invention is an improved insertable medical device useful for surgical insertion into a subject's body, wherein the improvement to the insertable medical device comprises an insertable medical device having a coating on its surface, wherein the coating comprises Cellular Factor-containing Solution (CFS) compositions dispersed in a polymeric coating material.

A third aspect of the invention is an improved transcutaneous medical device useful for insertion into a subject's body, wherein the improvement to the transcutaneous medical device comprises an transcutaneous medical device having a coating on its surface, wherein the coating comprises Cellular Factor-containing Solution (CFS) compositions dispersed in a polymeric coating material.

A fourth aspect of the invention is a method for downregulating the inflammatory response that occurs following the implantation, insertion or transcutaneous placement of a medical device in a patient, the method comprising the step of coating the medical device with a composition comprising Cellular Factor-containing Solution (CFS) compositions dispersed in a polymeric coating material.

In a specific embodiment of aspects one-four of the invention, the CFS composition is Amnion-derived Cellular Cytokine Solution (ACCS).

In a specific embodiment of aspects one-four of the invention, the CFS composition, including ACCS, is lyophilized prior to dispersal in the polymeric coating material.

In another specific embodiment of aspects one-four of the invention, the ACCS comprises physiological levels of VEGF, PDGF, Angiogenin, TGFβ2, TIMP-1 and TIMP-2.

In a particular embodiment of aspects one-four of the invention, the physiological levels are about 5.0-16 ng/mL for VEGF, about 3.5-4.5 ng/mL for Angiogenin, about 100-165 pg/mL for PDGF, about 2.5-2.7 ng/mL for TGFβ2, about 0.68 μg/mL for TIMP-1 and about 1.04 μg/mL for TIMP-2.

Still another embodiment of aspects one-four of the invention is wherein the medical device is selected from the group consisting of stents, joint replacement devices, tooth replacement devices, bone screws, bone repair rods, bone repair plates, bone repair wires, bone repair pins, spine screws, spine rods, artificial intervertebral discs, pacemakers, shunts, contact lenses, sutures, implantable defibrillators, cochlear implants and dental implants.

Another embodiment of aspects one-four of the invention is wherein the subject is a human subject or a non-human animal subject.

FIGURE LEGENDS

FIG. 1—Sustained-release of ACCS from Zimaloy® prosthetic hip replacement device and from a section of a Dacron® vascular graft.

DEFINITIONS

As defined herein "isolated" refers to material removed from its original environment and is thus altered "by the hand of man" from its natural state.

As used herein, "enriched" means to selectively concentrate or to increase the amount of one or more materials by elimination of the unwanted materials or selection and separation of desirable materials from a mixture (i.e. separate cells with specific cell markers from a heterogeneous cell population in which not all cells in the population express the marker).

As used herein, the term "substantially purified" means a population of cells substantially homogeneous for a particular marker or combination of markers. By substantially homogeneous is meant at least 90%, and preferably 95% homogeneous for a particular marker or combination of markers.

The term "placenta" as used herein means both preterm and term placenta.

As used herein, the term "totipotent cells" shall have the following meaning. In mammals, totipotent cells have the potential to become any cell type in the adult body; any cell type(s) of the extraembryonic membranes (e.g., placenta). Totipotent cells are the fertilized egg and approximately the first 4 cells produced by its cleavage.

As used herein, the term "pluripotent stem cells" shall have the following meaning Pluripotent stem cells are true stem cells with the potential to make any differentiated cell in the body, but cannot contribute to making the components of the extraembryonic membranes which are derived from the trophoblast. The amnion develops from the epiblast, not the trophoblast. Three types of pluripotent stem cells have been confirmed to date: Embryonic Stem (ES) Cells (may also be totipotent in primates), Embryonic Germ (EG) Cells, and Embryonic Carcinoma (EC) Cells. These EC cells can be isolated from teratocarcinomas, a tumor that occasionally occurs in the gonad of a fetus. Unlike the other two, they are usually aneuploid.

As used herein, the term "multipotent stem cells" are true stem cells but can only differentiate into a limited number of types. For example, the bone marrow contains multipotent stem cells that give rise to all the cells of the blood but may not be able to differentiate into other cells types.

As used herein, the term "extraembryonic cytokine-secreting cells" or "ECS cells" means a population of cells derived from the extraembryonic tissue which have the characteristic of secreting VEGF, Angiogenin, PDGF and TGFβ2 and the MMP inhibitors TIMP-1 and/or TIMP-2 at physiologically relevant levels in a physiologically relevant temporal manner into the extracellular space or into the surrounding culture media. ECS cells have not been cultured in the presence of any non-human animal materials, making them and cell products derived from them suitable for human clinical use as they are not xeno-contaminated. ECS cells may be selected from populations of cells and compositions described in this application and in US2003/0235563, US2004/0161419, US2005/0124003, U.S. Provisional Application Nos. 60/666,949, 60/699,257, 60/742,067, 60/813,759, U.S. application Ser. No. 11/333,849, U.S. application Ser. No. 11/392,892, PCTUS06/011392, US2006/0078993, PCT/US00/40052, U.S. Pat. No. 7,045,148, US2004/0048372, and US2003/0032179, the contents of which are incorporated herein by reference in their entirety. ECS cells have previously been referred to as TSE cells.

As used herein, the term "Amnion-derived Multipotent Progenitor cell" or "AMP cell" means a specific population of cells that are epithelial cells derived from the amnion. AMP cells have the following characteristics. They have not been cultured in the presence of any non-human animal materials, making them and cell products derived from them suitable for human clinical use as they are not xeno-contaminated. AMP cells are cultured in basal medium supplemented with human serum albumin. In a preferred embodiment, the AMP cells secrete the cytokines VEGF, Angiogenin, PDGF and TGFβ2 and the MMP inhibitors TIMP-1 and/or TIMP-2. The physiological range of the cytokine or cytokines in the unique combination is as follows: about 5-16 ng/mL for VEGF, about 3.5-4.5 ng/mL for Angiogenin, about 100-165 pg/mL for PDGF, about 2.5-2.7 ng/mL for TGFβ2, about 0.68 µg/mL for TIMP-1 and about 1.04 µg/mL for TIMP-2. The AMP cells may optionally express Thymosin β4. AMP cells grow without feeder layers, do not express the protein telomerase and are non-tumorigenic. AMP cells do not express the hematopoietic stem cell marker CD34 protein. The absence of CD34 positive cells in this population indicates the isolates are not contaminated with hematopoietic stem cells such as umbilical cord blood or embryonic fibroblasts. Virtually 100% of the cells react with antibodies to low molecular weight cytokeratins, confirming their epithelial nature. Freshly isolated amnion-derived cells, from which AMP cells are isolated, will not react with antibodies to the stem/progenitor cell markers c-kit (CD117) and Thy-1 (CD90). Several procedures used to obtain cells from full term or pre-term placenta are known in the art (see, for example, US 2004/0110287; Anker et al., 2005, Stem Cells 22:1338-1345; Ramkumar et al., 1995, Am. J. Ob. Gyn. 172:493-500). However, the methods used herein provide improved compositions and populations of cells.

By the term "animal-free" when referring to certain compositions, growth conditions, culture media, etc. described herein, is meant that no non-human animal-derived materials, such as bovine serum, proteins, lipids, carbohydrates, nucleic acids, vitamins, etc., are used in the preparation, growth, culturing, expansion, storage or formulation of the certain composition or process. By "no non-human animal-derived materials" is meant that the materials have never been in or in contact with a non-human animal body or substance so they are not xeno-contaminated. Only clinical grade materials, such as recombinantly produced human proteins, are used in the preparation, growth, culturing, expansion, storage and/or formulation of such compositions and/or processes.

By the term "expanded", in reference to cell compositions, means that the cell population constitutes a significantly higher concentration of cells than is obtained using previous methods. For example, the level of cells per gram of amniotic tissue in expanded compositions of AMP cells is at least 50 and up to 150 fold higher than the number of amnion epithelial cells in the primary culture after 5 passages, as compared to about a 20 fold increase in such cells using previous methods. In another example, the level of cells per gram of amniotic tissue in expanded compositions of AMP cells is at least 30 and up to 100 fold higher than the number of amnion epithelial cells in the primary culture after 3 passages. Accordingly, an "expanded" population has at least a 2 fold, and up to a 10 fold, improvement in cell numbers per gram of amniotic tissue over previous methods. The term "expanded" is meant to cover only those situations in which a person has intervened to elevate the number of the cells.

As used herein, the term "passage" means a cell culture technique in which cells growing in culture that have attained confluence or are close to confluence in a tissue culture vessel are removed from the vessel, diluted with fresh culture media (i.e. diluted 1:5) and placed into a new tissue culture vessel to allow for their continued growth and viability. For example, cells isolated from the amnion are referred to as primary cells. Such cells are expanded in culture by being grown in the growth medium described herein. When such primary cells are subcultured, each round of subculturing is referred to as a passage. As used herein, "primary culture" means the freshly isolated cell population.

As used herein, "conditioned medium" is a medium in which a specific cell or population of cells has been cultured, and then removed. When cells are cultured in a medium, they may secrete cellular factors that can provide support to or affect the behavior of other cells. Such factors include, but are not limited to hormones, cytokines, extracellular matrix (ECM), proteins, vesicles, antibodies, chemokines, receptors, inhibitors and granules. The medium containing the cellular factors is the conditioned medium. Examples of methods of preparing conditioned media are described in U.S. Pat. No. 6,372,494 which is incorporated by reference in its entirety herein.

As used herein, the term "Amnion-derived Cellular Cytokine Solution" or "ACCS" means conditioned medium that has been derived from AMP cells that have been cultured in basal media supplemented with human serum albumin and recombinant human EGF.

The term "physiological level" as used herein means the level that a substance in a living system is found and that is relevant to the proper functioning of a biochemical and/or biological process.

As used herein, the term "solution" as used in "Amnion-derived Cellular Cytokine Solution" means a liquid containing dispersed components, i.e. cytokines. The dispersed components may be fully solubilized, partially solubilized, suspended or otherwise dispersed in the liquid. Suitable liquids include, but are not limited to, water, osmotic solutions such as salt and/or sugar solutions, cell culture media, and other aqueous or non-aqueous solutions.

The term "lysate" as used herein refers to the composition obtained when cells, for example, AMP cells, are lysed and optionally the cellular debris (e.g., cellular membranes) is removed. This may be achieved by mechanical means, by freezing and thawing, by sonication, by use of detergents, such as EDTA, or by enzymatic digestion using, for example, hyaluronidase, dispase, proteases, and nucleases. In some instances, it may be desirable to lyse the cells and retain the cellular membrane portion and discard the remaining portion of the lysed cells.

As used herein, the term "pooled" means a plurality of compositions that have been combined to create a new composition having more constant or consistent characteristics as compared to the non-pooled compositions. For example, pooled ACCS have more constant or consistent characteristics compared to non-pooled ACCS. Examples of pooled compositions include "SP pools" (more than one ACCS collection/one placenta), "MP1 pools" (one ACCS collection/placenta, multiple placentas), and "MP2 pools" (more than one ACCS collection/placenta, multiple placentas).

As used herein, the term "substrate" means a defined coating on a surface that cells attach to, grown on, and/or migrate on. As used herein, the term "matrix" means a substance that cells grow in or on that may or may not be defined in its components. The matrix includes both biological and non-biological substances. As used herein, the term "scaffold" means a three-dimensional (3D) structure (substrate and/or matrix) that cells grow in or on. It may be composed of biological components, synthetic components or a combination of both. Further, it may be naturally constructed by cells or artificially constructed. In addition, the scaffold may contain components that have biological activity under appropriate conditions.

The term "cell product" or "cell products" as used herein refers to any and all substances made by and secreted from a cell, including but not limited to, protein factors (i.e. growth factors, differentiation factors, engraftment factors, cytokines, morphogens, proteases (i.e. to promote endogenous cell delamination, protease inhibitors), extracellular matrix components (i.e. fibronectin, etc.).

As used herein, the term "inflammatory response-modulating cytokines and growth factors" means physiologically relevant cytokines and growth factors that are capable of preventing and/or down-regulating the inflammatory response associated with virtually all medical device implants.

The term "therapeutically effective amount" means that amount of a therapeutic agent necessary to achieve a desired physiological effect (i.e. prevent and/or down-regulate an inflammatory response associated with an implanted/inserted medical device).

As used herein, the term "pharmaceutically acceptable" means that the components, in addition to the therapeutic agent, comprising the formulation, are suitable for administration to the patient being treated in accordance with the present invention.

As used herein, the term "therapeutic protein" includes a wide range of biologically active proteins including, but not limited to, growth factors, enzymes, hormones, cytokines, inhibitors of cytokines, blood clotting factors, peptide growth and differentiation factors.

As used herein, the term "tissue" refers to an aggregation of similarly specialized cells united in the performance of a particular function.

As used herein, the terms "a" or "an" means one or more; at least one.

As used herein, the term "adjunctive" means jointly, together with, in addition to, in conjunction with, and the like.

As used herein, the term "co-administer" can include simultaneous or sequential administration of two or more agents.

As used herein, the term "agent" means an active agent or an inactive agent. By the term "active agent" is meant an agent that is capable of having a physiological effect when administered to a subject. Non-limiting examples of active agents include growth factors, cytokines, antibiotics, cells, conditioned media from cells, etc. By the term "inactive agent" is meant an agent that does not have a physiological effect when administered. Such agents may alternatively be called "pharmaceutically acceptable excipients". Non-limiting examples include time-release capsules and the like.

The terms "parenteral administration" and "administered parenterally" are art-recognized and refer to modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intra-articulare, subcapsular, subarachnoid, intraspinal, epidural, intracerebral and intrasternal injection or infusion.

The term "enteral administration" and "administered enterally" are art-recognized and refer to modes of administration other than enteral and topical administration, usually by oral or rectal routes.

The term "topical administration" and "administered topically" are art-recognized and refer to modes of administration other than parenteral and enteral administration, usually by application to the skin.

The term "adsorb" as used herein refers to the act of a liquid, gas, or a dissolved substance accumulating on the surface of a solid.

The terms "sustained-release", "extended-release", "time-release", "controlled-release", or "continuous-release" as used herein means an agent, typically a therapeutic agent or drug, that is released over time.

The terms "bioerodable" or "bioerosion" as used herein mean a combination of physical (i.e. dissolution) and chemical (i.e. chemical bond cleavage) processes that result in the breakdown of a substance.

The term "biodegradable" or "biodegradation" as used herein means a biological agent (i.e. an enzyme, microbe or cell) is responsible for the breakdown of a substance.

The terms "bioresporbable" or "bioabsorptable" as used herein mean the removal of a breakdown product by cellular activity (i.e. phagocytosis). The term "nonabsorbable" as used herein means that a substance is not broken down by a chemical process.

As used herein, the term "medical device" means an instrument, apparatus, implant, in vitro reagent, or similar or related article that is used to diagnose, prevent, or treat disease or other conditions, and does not achieve its purposes through chemical action within or on the body (which would make it a drug). Medical device includes implanted medical device, implantable medical device, inserted medical device, insertable medical device, and medical devices placed on a body surface (i.e., on skin, cornea, etc.).

As used herein, the term "transcutaneous medical device" means a medical device that is implanted in the body and exits externally through the skin.

"Treatment," "treat," or "treating," as used herein covers any treatment of a disease or condition of a mammal, particularly a human, and includes: (a) preventing the disease or condition from occurring in a subject which may be predisposed to the disease or condition but has not yet been diagnosed as having it; (b) inhibiting the disease or condition, i.e., arresting its development; (c) relieving and or ameliorating the disease or condition, i.e., causing regression of the disease or condition; or (d) curing the disease or condition, i.e., stopping its development or progression. The population of subjects treated by the methods of the invention includes subjects suffering from the undesirable condition or disease, as well as subjects at risk for development of the condition or disease.

As used herein, a "wound" is any disruption, from whatever cause, of normal anatomy (internal and/or external anatomy) including but not limited to traumatic injuries such as mechanical (i.e. contusion, penetrating), thermal, chemical, electrical, concussive and incisional injuries; elective injuries such as operative surgery and resultant incisional hernias, fistulas, etc.; acute wounds, chronic wounds, infected wounds, and sterile wounds, as well as wounds associated with disease states (i.e. ulcers caused by diabetic neuropathy or ulcers of the gastrointestinal or genitourinary tract). A wound is dynamic and the process of healing is a continuum requiring a series of integrated and interrelated cellular processes that begin at the time of wounding and proceed beyond initial wound closure through arrival at a stable scar. These cellular processes are mediated or modulated by humoral substances including but not limited to cytokines, lymphokines, growth factors, and hormones. In accordance with the subject invention, "wound healing" refers to improving, by some form of intervention, the natural cellular processes and humoral substances of tissue repair such that healing is faster, and/or the resulting healed area has less scaring and/or the wounded area possesses tissue strength that is closer to that of uninjured tissue and/or the wounded tissue attains some degree of functional recovery.

As used herein the term "standard animal model" refers to any art-accepted animal model in which the compositions of the invention exhibit efficacy.

DETAILED DESCRIPTION

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It must be noted that as used herein and in the appended claims, the singular forms "a," "and" and "the" include plural references unless the context clearly dictates otherwise.

The anti-inflammatory properties of Amnion-derived Cytokine Solution (ACCS) are currently being used to assist in wound healing in human clinical trials. ACCS contains more than 200 proteins, cytokines, and growth factors in solution and has been shown to reduce inflammation in several animal models (see Example below). In addition, ACCS is presently being tested in several human clinical trials involving inflammation resulting from radiation burns and skin grafts in diabetic patients being treated for burns.

As described above, implantation of any medical device results local inflammation at the implant site. In the case of coronary stents, leukocyte recruitment and infiltration occur at sites of vascular injury where the endothelial cells lining the vessels have been denuded and platelets and fibrin have been deposited. In vivo studies have shown that leukocytes and platelets co-localize at sites of hemorrhage, within atherosclerotic and post-angioplasty restenotic lesions, and in areas of ischemia/reperfusion injury. This interaction between platelets and leukocytes appears to be critical to the inflammatory response. Monocyte chemo-attractant protein (MCP)-1 participates in the recruitment of monocytes as well as basophils and certain activated T cells. Interleukin (IL)-8, plays a critical role in the recruitment of leukocytes to areas of vascular injury. It is well known that IL-8 is a pivotal cytokine in the recruitment of neutrophils. The nonspecific inflammatory marker, C-reactive protein, has been shown to be up-regulated after stent placement.

This invention is directed to the incorporation of CFS compositions, including ACCS, into or onto any or all implantable/insertable/transcutaneous medical devices in order to effect the sustained delivery of CFS compositions, including ACCS, and their anti-inflammatory properties at the implantation/insertion site. This novel improvement to the medical devices will impart greater biocompatibility and safety to these devices.

The CFS composition, including ACCS, maybe coated directly onto the medical devices or suspended in a polymer solution formed by dissolving a pharmaceutically acceptable polymer (e.g. ethylene vinyl acetate copolymer, EVAc) in a volatile organic solvent such as dichloromethane. The medical device is then submerged into the polymer coating and removed. The organic solvent is allowed to evaporate, leaving a polymer coating containing the polymer with the CFS compositions' proteins, including ACCS proteins, dispersed in dry powdered form within the coating. Such a CFS composition/polymer coating would be capable of sustained-delivery of the CFS composition from the medical devices. Furthermore, as the CFS composition incorporated into or onto the medical devices will be in lyophilized or freeze-dried form, the release of the CFS composition will only occur upon contact with an aqueous solution capable of solubilizing and releasing the CFS composition.

It is also possible to coat any such medical device by spraying the CFS composition/polymer solution onto the medical device and allowing the organic solvent to evaporate.

Therefore, local absorption of a CFS composition, including ACCS, from the coated medical device would be expected to effectively deliver the 200 proteins, cytokines, and growth factors, including inflammatory-response modulating growth factors and cytokines, to the sites of inflammation associated with implantation/insertion of a medical device in a sustained fashion. It should be understood that the release kinetics of the CFS compositions from the coating can be altered by adjusting the drug loading, drug particle size, device geometry, etc. in order to achieve first order, zero order or other release kinetic profiles.

Obtaining and Culturing of Cells

ECS Cells—

Various methods for isolating cells from extraembryonic tissue, which may then be used to produce the ECS cells of the instant invention are described in the art (see, for example, US2003/0235563, US2004/0161419, US2005/0124003, U.S. Provisional Application Nos. 60/666,949, 60/699,257, 60/742,067, 60/813,759, U.S. application Ser. No. 11/333, 849, U.S. application Ser. No. 11/392,892, PCTUS06/011392, US2006/0078993, PCT/US00/40052, U.S. Pat. No. 7,045,148, US2004/0048372, and US2003/0032179).

Identifying ECS Cells—

Once extraembryonic tissue is isolated, it is necessary to identify which cells in the tissue have the characteristics associated with ECS cells (see definition above). For example, cells are assayed for their ability to secrete VEGF, Angiogenin, PDGF and TGFβ2 and the MMP inhibitors TIMP-1 and/or TIMP-2 into the extracellular space or into surrounding culture media. In some instances, it may be difficult or impossible to detect certain factors using standard assays. This may be because certain factors are secreted by the cells at physiological levels that are below the level of detection by the assay methods. It may also be that the factor(s) is being utilized by the ECS cell and/or by other local cells, thus preventing accumulation at detectable levels using standard assays. It is also possible that the temporal manner in which the factors are secreted may not coincide with the timing of sampling.

AMP cell compositions are prepared using the steps of a) recovery of the amnion from the placenta, b) dissociation of the epithelial cells from the amniotic membrane using a protease, c) culturing of the cells in a basal medium with the addition of a naturally derived or recombinantly produced human protein (i.e. human serum albumin) and no non-human animal protein; d) selecting AMP cells from the epithelial cell culture, and optionally e) further proliferation of the cells, optionally using additional additives and/or growth factors (i.e. recombinant human EGF). Details are contained in U.S. Pat. No. 8,278,095, issued Oct. 2, 2012, U.S. Pat. No. 8,058,066, issued Nov. 15, 2011 and U.S. Pat. No. 8,088,732, issued Jan. 3, 2012, all of which are incorporated herein by reference.

Culturing of the AMP Cells—

The cells are cultured in a basal medium. Such medium includes, but is not limited to, EPILIFE® culture medium for epithelial cells (Cascade Biologicals), OPTI-PRO™ serum-free culture medium, VP-SFM serum-free medium, IMDM highly enriched basal medium, KNOCKOUT™ DMEM low osmolality medium, 293 SFM II defined serum-free medium (all made by Gibco; Invitrogen), HPGM hematopoietic progenitor growth medium, Pro 293S-CDM serum-free medium, Pro 293A-CDM serum-free medium, UltraMDCK™ serum-free medium (all made by Cambrex), STEMLINE® T-cell expansion medium and STEMLINE® II hematopoietic stem cell expansion medium (both made by Sigma-Aldrich), DMEM culture medium, DMEM/F-12 nutrient mixture growth medium (both made by Gibco), Ham's F-12 nutrient mixture growth medium, M199 basal culture medium (both made by Sigma-Aldrich), and other comparable basal media. Such media should either contain human protein or be supplemented with human protein. As used herein a "human protein" is one that is produced naturally or one that is produced using recombinant technology. "Human protein" also is meant to include a human derivative or preparation thereof, such as human serum, which contains human protein. In specific embodiments, the basal media is IMDM highly enriched basal medium, STEMLINE® T-cell expansion medium or STEMLINE® II hematopoietic stem cell expansion medium, or OPTI-PRO™ serum-free culture medium, or combinations thereof and the human protein is human serum albumin is at least 0.5% and up to 10%. In particular embodiments, the human serum albumin is from about 0.5 to about 2%. In a specific embodiment the human albumin is at 0.5%. The human albumin may come from a liquid or a dried (powder) form and includes, but is not limited to, recombinant human serum albumin, PLASBUMIN® normal human serum albumin and PLASMANATE® human blood fraction (both made by Talecris Biotherapeutics).

The invention further contemplates the use of any of the above basal media wherein animal-derived proteins are replaced with recombinant human proteins and animal-derived serum, such as BSA, is replaced with human serum albumin. In preferred embodiments, the media is serum-free in addition to being animal-free.

Optionally, other factors are used. In one embodiment, epidermal growth factor (EGF) at a concentration of between 0-1 µg/mL is used. In a preferred embodiment, the EGF concentration is around 10-20 ng/mL. All supplements are clinical grade.

Generation of CFS Compositions, Including ACCS

ECS conditioned medium—is obtained as described below for ACCS, except that ECS cells are used.

Generation of ACCS—

The AMP cells of the invention can be used to generate ACCS. In one embodiment, the AMP cells are isolated as described herein and $1\times10^6$ cells/mL are seeded into T75 flasks containing between 5-30 mL culture medium, preferably between 10-25 mL culture medium, and most preferably about 10 mL culture medium. The cells are cultured until confluent, the medium is changed and in one embodiment the ACCS is collected 1 day post-confluence. In another embodiment the medium is changed and ACCS is collected 2 days post-confluence. In another embodiment the medium is changed and ACCS is collected 4 days post-confluence. In another embodiment the medium is changed and ACCS is collected 5 days post-confluence. In a preferred embodiment the medium is changed and ACCS is collected 3 days post-confluence. In another preferred embodiment the medium is changed and ACCS is collected 3, 4, 5, 6 or more days post-confluence. Skilled artisans will recognize that other embodiments for collecting ACCS from AMP cell cultures, such as using other tissue culture vessels, including but not limited to cell factories, flasks, hollow fibers, or suspension culture apparatus, or collecting ACCS from sub-confluent and/or actively proliferating cultures, are also contemplated by the methods of the invention. It is also contemplated by the instant invention that the ACCS be cryopreserved following collection. It is also contemplated by the invention that ACCS be lyophilized following collection. It is also contemplated by the invention that ACCS be formulated for sustained-release following collection. Skilled artisans are familiar with cryopreservation lyophilization, and sustained-release formulation methodologies.

The ACCS of the invention is characterized by assaying for physiologically relevant cytokines secreted in the physiologically relevant range of about 5-16 ng/mL for VEGF, about 3.5-4.5 ng/mL for Angiogenin, about 100-165 pg/mL for PDGF, about 2.5-2.7 ng/mL for TGFβ2, about 0.68 µg/mL for TIMP-1 and about 1.04 µg/mL for TIMP-2.

It is also contemplated by the invention that ACCS, including pooled ACCS, be concentrated prior to use. The appropriate level of concentration required will be dependent upon the intended use and therefore will need to be empirically determined.

The compositions of the invention can be prepared in a variety of ways depending on the intended use of the compositions. For example, a composition useful in practicing the invention may be a liquid comprising an agent of the invention, i.e. CFS compositions, including ACCS, in solution, in suspension, or both (solution/suspension). The term "solution/suspension" refers to a liquid composition where a first portion of the active agent is present in solution and a second portion of the active agent is present in particulate form, in suspension in a liquid matrix. A liquid composition also includes a gel. The liquid composition may be aqueous or in the form of an ointment, salve, cream, or the like.

An aqueous suspension or solution/suspension useful for practicing the methods of the invention may contain one or more polymers as suspending agents. Useful polymers include water-soluble polymers such as cellulosic polymers and water-insoluble polymers such as cross-linked carboxyl-containing polymers. Protein based polymers such as gelatin are also contemplated as useful matrix forming materials. An aqueous suspension or solution/suspension of the present invention is preferably viscous or muco-adhesive, or even more preferably, both viscous and muco-adhesive. Hydrophobic crystalline or amorphous polymers such as ethylene vinyl acetate copolymer (EVAc) maybe useful as a matrix forming materials. Polymers such as polylactic acid (PLA), polycaprolactone, polylactide/glycolide (PLGA), polyorthoesters, polyanhydrides etc. are examples of biodegradable polymers that may be useful matrix forming materials.

Alternative Formulation of CFS Compositions, Including ACCS

The CFS compositions, including ACCS, may be formulated as sustained-release/controlled-release/timed-release/extended-release compositions. Skilled artisans are familiar with methodologies to create such compositions of therapeutic agents, including protein-based therapeutic agents such as CFS compositions, including ACCS. Sustained-release/controlled-release/timed-release CFS compositions, including ACCS, may be made by any of the methods described herein, as well. In addition, other sustained-release methodologies familiar to skilled artisans, while not specifically described herein, are also suitable for use with the CFS compositions, including ACCS.

Pharmaceutical Compositions—

The present invention provides pharmaceutical compositions of CFS compositions, including ACCS, and a pharmaceutically acceptable carrier. The term "pharmaceutically acceptable" means approved by a regulatory agency of the Federal or a state government or other country's regulatory agency, or listed in the U.S. Pharmacopeia or other generally recognized pharmacopeia for use in animals, and more particularly, in humans. The term "carrier" refers to a diluent, adjuvant, excipient, or vehicle with which the composition is administered. Such pharmaceutical carriers can be sterile liquids, such as water and oils, including those of petroleum, animal, vegetable or synthetic origin, such as peanut oil, soybean oil, mineral oil, sesame oil, biocompatible polymers such as ethylene vinyl acetate copolymer, polylactic acid, polylactide/glycolide, polyhydroxymethyl methacrylate, carboxymethyl cellulose, polyethylene glycol, poloxamer, and the like. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. Examples of suitable pharmaceutical carriers are described in "Remington's Pharmaceutical Sciences" by E. W. Martin, and still others are familiar to skilled artisans.

The pharmaceutical compositions of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

One of skill in the art may readily determine the appropriate concentration, or dose, of the CFS compositions, including ACCS, for a particular purpose. The skilled artisan will recognize that a preferred dose is one which produces a therapeutic effect, such as preventing and/or down-regulating the inflammatory response associated with the implantation, insertion or transcutaneous placement of a medical device, in a patient. Of course, proper doses of the CFS compositions, including ACCS, will require empirical determination at time of use based on several variables including but not limited to the type of medical device being used; patient age, weight, sex, health; other medications and treatments being administered to the patient; and the like.

In further embodiments of the present invention, it may be desirable to co-administer other agents, including active agents and/or inactive agents, with the coated medical device. Active agents include but are not limited to cytokines, chemokines, antibodies, inhibitors, antibiotics, anti-fungals, anti-virals, immunosuppressive agents, and the like. Inactive agents include carriers, diluents, stabilizers, gelling agents, thickening agents (i.e. human serum albumin, hyaluronic acid), delivery vehicles, ECMs (natural and synthetic), scaffolds, collagen, and the like. When the medical device is administered conjointly with other pharmaceutically active agents, even less of the CFS compositions, including ACCS, on the medical device may be needed to be therapeutically effective.

Skilled artisans will recognize that any and all of the standard methods and modalities for implanting, inserting or transcutaneous placement of medical devices currently in clinical practice and clinical development are suitable for practicing the methods of the invention. Routes of administration, formulation, co-administration with other agents (if appropriate) and the like are discussed in detail elsewhere herein.

Exemplary Therapeutic Uses of a Coated Medical Device

Artificial Eye Lenses (Pseudophakos), number of procedures: 2.582 million, total annual expenditure: $8 billion-$10 billion, average cost per eye: $3,200-$4,500, depending on lens type. Major manufacturers include Alcon Laboratories/Novartis, Abbott Laboratories, and Bausch & Lomb.

Ear Tubes (Tympanostomy Tubes), number of procedures: 715,000, total annual expenditure: $1 billion-$2 billion, average cost per procedure: $1,000-$4,500.

Coronary Stents, number of procedures: 560,000, total annual expenditure: $7.5 billion, average cost per procedure: $13,000. Major manufacturers include Boston Scientific and Abbott Laboratories.

Artificial Knees, number of procedures: 543,000, total annual expenditure: $12 billion, average cost per procedure: $22,000. Major manufacturers include Zimmer, Depuy/J&J, Stryker, and Biomet, Smith & Nephew Metal Screws, Pins, Plates, and Rods (Traumatic Fracture Repair), number of procedures: 453,000, total annual expenditure: $4.5 billion, average cost per procedure: $2,000-$20,000. Major manufacturer includes Synthes.

IUDs (Intra-Uterine Devices), number of procedures: 425,000, total annual expenditure: $340 million, average cost per procedure: $800. Major manufacturers include Teva Pharmaceutical Industries and Bayer HealthCare.

Implantable Dental Devices, number of procedures: 2 million dental implants, total annual expenditure: $6 billion, average cost per procedure: $2,500, Major players: Nobel Biocare and Straumann.

Spine Screws, Rods, and Artificial Discs (Spinal Fusion Hardware), number of procedures: 413,000, total annual expenditure: $10 billion, average cost per procedure: $25,000. Major manufacturer includes Medtronic.

Breast Implants, number of procedures: 366,000, total annual expenditure: $992 million, average cost per procedure: $3,351. Major manufacturers include Allergan and Mentor.

Heart Pacemakers, number of procedures: 235,567, total annual expenditure: $4.5 billion, average cost per procedure: $20,000. Major manufacturers include Medtronic, St. Jude Medical, and Boston Scientific.

Artificial Hips, number of procedures: 230,000, total annual expenditure: $10.5 billion, average cost per procedure: $45,000. Major manufacturers include Zimmer, Stryker, DePuy/J&J, Biomet, and Wright Medical.

Implantable Cardioverter Defibrillators, number of procedures: 133,262, total annual expenditure: $5.5 billion, average cost per procedure: $40,000. Major manufacturers include Medtronic, St. Jude Medical, and Boston Scientific.

Contact lenses, staples and other devices not explicitly mentioned are also contemplated by the invention described herein.

EXAMPLES

The following examples are put forth so as to provide those of ordinary skill in the art with a complete disclosure and description of how to make and use the compositions and methods of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees centigrade, and pressure is at or near atmospheric.

Example 1

Preparation of AMP Cell Compositions

Amnion epithelial cells were dissociated from starting amniotic membrane using the dissociation agents PXXIII. The average weight range of an amnion was 18-27 g. The number of cells recovered per g of amnion was about $10-15 \times 10^6$ for dissociation with PXXIII.

Method of Obtaining Selected AMP Cells—

Amnion epithelial cells were plated immediately upon isolation from the amnion. After ~2 days in culture non-adherent cells were removed and the adherent cells were kept. This attachment to a plastic tissue culture vessel is the selection method used to obtain the desired population of AMP cells. Adherent and non-adherent AMP cells appear to have a similar cell surface marker expression profile but the adherent cells have greater viability and are the desired population of cells. Adherent AMP cells were cultured in basal medium supplemented with human serum albumin until they reached 120,000-150,000 cells/cm$^2$. At this point, the cultures were confluent. Suitable cell cultures will reach this number of cells between ~5-14 days. Attaining this criterion is an indicator of the proliferative potential of the AMP cells and cells that do not achieve this criterion are not selected for further analysis and use. Once the AMP cells reached ~120,000-150,000 cells/cm$^2$, they were collected and cryopreserved. This collection time point is called p0.

Example 2

Generation of ACCS

The AMP cells of the invention can be used to generate ACCS, including pooled ACCS. The AMP cells were isolated as described above and about $1 \times 10^6$ cells/mL were seeded into T75 flasks containing ~10 mL culture medium as described above. The cells were cultured until confluent, the medium was changed and ACCS was collected 3 days post-confluence. Optionally, the ACCS is collected again after 3 days, and optionally again after 3 days. Skilled artisans will recognize that other embodiments for collecting ACCS from confluent cultures, such as using other tissue culture vessels, including but not limited to cell factories, flasks, hollow fibers, or suspension culture apparatus, etc. are also contemplated by the methods of the invention (see Detailed Description above). It is also contemplated by the instant invention that the ACCS be cryopreserved, lyophilized, irradiated or formulated for sustained-release following collection. It is also contemplated that ACCS be collected at different time points (see Detailed Description for details).

Example 3

Generation of Pooled ACCS

ACCS was obtained essentially as described above. In certain embodiments, ACCS was collected multiple times from an AMP culture derived from one placenta and these multiple ACCS collections were pooled together. Such pools are referred to as "SP pools" (more than one ACCS collection/one placenta). In another embodiment, AMP cultures were derived from several placentas, i.e. from 5 or 10 placentas. The AMP cells from each placenta were cultured and one ACCS collection from each culture was collected and then they were all pooled. These pools are termed "MP1 pools" (one ACCS collection/placenta, multiple placentas). In yet another embodiment, AMP cell cultures were derived from several placentas, i.e. from 5 or 10 placentas. The AMP cells from each placenta were cultured and more than one ACCS collection was performed from each AMP cell culture and then pooled. These pools are termed "MP2 pools" (more than one ACCS collection/placenta, multiple placentas).

Example 4

Release of ACCS from an Implantable Medical Device

Preparation of ACCS polymer suspension: Ethylene vinyl acetate copolymer (ELVAX 40W, DuPont, Wilmington, Del.) was dissolved in dichloromethane to form a 10% (wt/vol) solution. Twenty-five mg of lyophilized ACCS was weighed and suspended in 2 mL of the polymer solution.

Experiment 1:

A portion of a Zimaloy® prosthetic replacement hip device was dipped into the ACCS-ethylene vinyl acetate copolymer suspension to partially coat the ball joint insertion end and the pointed end of the device. The device was then removed and the polymer coating dried overnight by the evaporation of the dichloromethane solvent. The coated portion of the device was then placed into a pH 7.4 phosphate buffered saline for release of ACCS proteins.

Experiment 2:

An approximately 1 cm×1 cm section was excised from a Dacron® vascular graft material. It was dipped into the ACCS-ethylene vinyl acetate copolymer suspension described above. The graft material was removed and the polymer coating dried overnight upon the evaporation of the dichloromethane solvent. The coated portion of the device was then placed into a pH 7.4 phosphate buffered saline for release of ACCS proteins.

Results of Experiment 1 and 2:

The results in FIG. 1 demonstrate the sustained cumulative release of micrograms of ACCS from the polymer coatings from the Zimaloy® prosthetic replacement hip device and from the Dacron® vascular graft over 48 hours. The coated Zimaloy® prosthetic replacement hip device released a cumulative total of approximately 1303 micrograms of ACCS proteins over the 48 hour time period tested as determined by the Bradford Protein Assay (Bradford, M. M. (1976), "Rapid and sensitive method for the quantitation of microgram quantities of protein utilizing the principle of protein-dye binding", Anal. Biochem. 72: 248-254). The coated Dacron® vascular graft material released a cumulative total of approximately 704 micrograms of ACCS proteins over the 48 hour period tested. The greater release from the Zimaloy® prosthetic replacement hip device is due to the greater surface area of the coating compared to the Dacron® vascular graft material. Furthermore, the ACCS incorporated into the ELVAX polymer coatings were shown to contain 23 representative ACCS analytes. Antibody array revealed the following proteins release from the Dacron® and Zymaloy® ELVAX/ACCS coated devices; PDGF-BB, sTNF RI, TRAIL R3, IGFBP-6, AXL, Amphiregulin, uPAR, PDGF AA, ErbB3, LYVE-1, FLRG, Adipsin/Factor D, Angiogenin, VEGF, DIPPIV, IGFBP-2, TIMP-2, TIMP-1, GDF-15, PAI-I, Decorin, CA125 and DKK-3.

Example 5

Coating of a Titanium Implant Wire with ACCS

ACCS was diafiltered using four Amicon® Ultra-15 centrifugal filter devices (EMD Millipore Corp., Billerica, Mass.) with 12 ml each. Buffer exchange was performed using Water for Injection (WFI) following the manufacturer's instructions. The filtered ACCS solution was frozen and lyophilized for coating.

A 5% Ethylene Vinyl Acetate (EVA) solution was prepared in dichloromethane. Lyophilized ACCS powder was added to the equivalent of 15% wt ACCS/wt ACCS plus polymer. This mixture was then used to coat five 10 cm length sections of titanium 6AI-4V (grade 5) implant wires. Five pre-chilled pieces of the titanium wire implants were dipped separately into the solution and allowed to dry overnight at room temperature. The pieces were weighed before and after coating and showed a total weight increase of approximately 1 mg. The coated wire implants together were placed in a test tube containing 150 µA of WFI and allowed to elute for 24 hrs at room temperature. Several collections of release media were performed after incubation times of 2 hrs, 6 hrs and 24 hrs.

Preliminary results demonstrated that 1329 pg/mL of DPPIV activity, a component of ACCS, was detected at 2 hrs. Not surprisingly, the 6 hr and 24 hr time points were below the level of detection with this particular assay of DPPIV activity. However, the presence of luminescence was detected at 2 hrs and 6 hrs indicating sustained release of ACCS from the EVAc coating (see Table 1 below).

TABLE 1

| Time (hours) | Average Luminescence |
| --- | --- |
| 0 | 0 |
| 2 | 7721 |
| 6 | 429 |

Additional, more sensitive assays such as antibody array for other ACCS proteins are currently being investigated.

Example 6

Retention of ACCS Bioactivity after Combination or Incorporation into Gelatin Film A 5% gelatin in ACCS was prepared by dissolving gelatin in an aqueous solution of ACCS at 40° C. for 15 min. Five percent gelatin in 1×PBS was also prepared as a control. Two hundred µl of 5% ACCS/gelatin was placed in a 1.5 mL centrifuge tube and allowed to air dry for 48 hrs at room temperature to form a transparent solid film. Control samples were also held at room temperature but were not allowed to dry. On the day of the assay, the dried ACCS/gelatin film was solubilized for 4 hrs with 180 µA of water for injection (WFI). Samples were then heated to 37° C. to solubilize the gels and then diluted into assay buffer and tested for DPPIV activity.

Table 2 below shows the results of the experiment comparing the DPPIV activity of ACCS/gelatin, dried and solubilized ACCS/gelatin film, a 95% solution of ACCS, and 5% Phosphate Buffered Saline (PBS)/gelatin negative control. The results showed that ACCS/gelatin retained its activity and that drying the solution did not reduce DPPIV activity.

TABLE 2

| Formulation | DPPIV activity (pg/mL) |
| --- | --- |
| ACCS/gelatin | 16,201 |
| Dried and solubilized ACCS/gelatin | 23,538 |
| 95% ACCS solution | 18,344 |
| 5% PBS/gelatin | 116 |

Example 7

Cumulative Release of 4 Representative ACCS Proteins from Titanium EVAc Coated Wires Measured by MSD Antibody Array Assay An experiment was performed to measure the cumulative release of 4 representative ACCS proteins from Titanium EVAc coated wires measured by MSD antibody array assay. As shown in Table 3 below, the cumulative release of four representative proteins from EVAc coated titanium wires was shown to increase over 24 hours. This indicates sustained release of these ACCS proteins from EVAc coated titanium wires.

TABLE 3

| | Protein | | | |
| --- | --- | --- | --- | --- |
| Time (hrs) | TIMP-1 (pg/mL) | GDF-15 (pg/mL) | PAI-1 (pg/mL) | DKK3 (pg/mL) |
| 2 | 248.52 | 60.01 | 1187.72 | 9221.26 |
| 6 | 277.68 | 62.49 | 1301.68 | 9501.24 |
| 24 | 298.89 | 62.49 | 1303.43 | 9503.03 |

Example 8

Cumulative Release of 4 Representative ACCS Proteins from Titanium Gelatin Coated Wires Measured by MSD Antibody Array Assay An experiment was performed to measure the cumulative release of 4 representative ACCS proteins from Titanium Gelatin coated wires measured by MSD antibody array assay. As shown in Table 4 below, the cumulative release of four representative proteins from Gelatin coated titanium wires was shown to increase over 7 hours. This indicates sustained release of these ACCS proteins from Gelatin coated titanium wires.

TABLE 4

| Time (hrs) | Protein | | | |
|---|---|---|---|---|
| | TIMP-1 (pg/mL) | GDF-15 (pg/mL) | PAI-1 (pg/mL) | DKK3 (pg/mL) |
| 2 | 1458.85 | 94.35 | 1332.60 | 48.18 |
| 4 | 1645.15 | 118.81 | 2516.20 | 75.65 |
| 7 | 1756.04 | 124.40 | 2905.85 | 120.19 |

Example 9

Inflammatory Model—Use of ACCS to Prevent Onset of Periodontal Disease in an Animal Model Objective:

The aim of this study was to evaluate the preventive role of ACCS in *Porphyromonas gingivalis* (*P. gingivalis*)-induced experimental periodontitis in rabbits Methods:

Eight New-Zealand White rabbits were distributed into 3 groups: 1. Untreated (n=2), 2. Control (unconditioned ACCS culture media) (n=3), and 3. ACCS (n=3). At baseline, all rabbits received silk ligatures bilaterally tied around mandibular second premolars under general anesthesia. The assigned test materials, ACCS or control, in volumes of 10 µL were topically applied to the ligated sites with a blunt needled-Hamilton Syringe from the time of ligature; control animals received ligature, but no treatment. Topical *P. gingivalis*-containing slurry (1 mL) was subsequently applied to induce the periodontal inflammation. The application of test materials and *P. gingivalis* continued for 6 weeks on an every-other-day schedule. At 6 weeks, following euthanasia, the mandibles were surgically harvested. Morphometric, radiographic and histologic evaluations were performed.

Results:

Macroscopic evaluations including soft tissue assessments, crestal bone and infrabony measurements showed significant periodontal breakdown induced by *P. gingivalis* in control and no treatment groups at 6 weeks compared to historical ligature-alone groups (p=0.05, p=0.03, respectively). ACCS application significantly inhibited soft tissue inflammation and prevented both crestal bone loss and infrabony defect formation compared to untreated and control groups (p=0.01, p=0.05, respectively). Histologic assessments and histomorphometric measurements supported the clinical findings; ACCS treated animals demonstrated significantly less inflammation in soft tissue and less bone loss compared to the untreated and control groups (p=0.05).

Conclusions:

Topical ACCS application prevents periodontal inflammatory changes and bone loss induced by *P. gingivalis* as shown both at clinical and histopathological level. ACCS has potential as a therapeutic approach for the prevention of periodontal diseases Example 10

Inflammatory Model—Use of ACCS to Stop Progression of or Reverse Periodontal Disease in an Animal Model Objective:

The aim of this study was to evaluate the therapeutic actions of ACCS in the treatment of periodontitis induced by *P. gingivalis*.

Methods:

The study was conducted using a two-phase rabbit periodontitis protocol: 1—Disease induction (6 weeks) and 2—Treatment (6 weeks). Periodontal disease was induced in 16 New-Zealand White rabbits by every-other-day application of topical *P. gingivalis* to ligatured mandibular premolars. At the end of Phase 1, 4 randomly selected rabbits were sacrificed to serve as the baseline disease group. For Phase 2, the remaining 12 rabbits were distributed into 3 groups (n=4), 1—Untreated, 2—Control (unconditioned ACCS culture media) and 3—ACCS treatment. At the end of Phase 2, morphometric, radiographic and histologic evaluations were performed on harvested mandibles.

Results:

The baseline disease group exhibited experimental periodontitis evidenced by tissue inflammation and bone loss. At the end of Phase 2, the untreated group showed significant disease progression characterized by increased soft and hard tissue destruction (p=0.05). The tissue inflammation and bone loss was significantly reduced by topical ACCS compared to baseline disease and untreated groups (p=0.05; p=0.002, respectively). The control treatment also arrested disease progression compared to untreated group (p=0.01), but there was no improvement in periodontal health compared to baseline disease (p=0.4). Histopathological assessments revealed similar findings; ACCS stopped the progression of inflammatory process (p=0.003) and reversed bone destruction induced by *P. gingivalis* (p=0.008). The ACCS-treated group had minimal osteoclastic activity limited to crestal area compared to untreated and control groups, which showed a profound osteoclastogenic activity at the bone crest as well as at interproximal sites.

Conclusions:

Topical application of ACCS stopped the progression of periodontal inflammation and resulted in tissue regeneration in rabbit periodontitis indicating its potential therapeutic efficacy.

Example 11

Inflammatory Model—Evaluate the Efficacy of Topically Applied ACCS to Inhibit Irritant 12-O-Tetradecanoylphorbol-3-Acetate (TPA) Skin Inflammation in Mice Method: Topical treatment was given twice daily to the following groups: 1. TPA+topical control; 2. TPA+ACCS; 3. TPA+clobetasol 0.05 topical solution (the strongest available topical corticosteroid); 4. ACCS alone; 5. No treatment (the other untreated ear was measured). The endpoints for the study were ear thickness and ear weight at the end of the experiment. The thicker the ear and the more it weighs correlates with the degree of inflammation.

Results: Topically applied ACCS was effective at reducing the inflammation induced by TPA. The anti-inflammatory activity of topical ACCS reached the same level as clobetasol (a class 1 potent topical corticosteroid) by 3 days after beginning application.

Conclusion: ACCS has a strong anti-inflammatory effect when applied to skin.

Example 12

Inflammatory Model—Evaluate the Efficacy of Intralesional Injection of ACCS to Inhibit Irritant (TPA) Skin Inflammation in Mice Method: Intralesional injection into the ear was given once daily to the following groups: 1. TPA+intralesional control; 2.

TPA+intralesional ACCS; 3. TPA+intralesional kenalog (10 mg/ml) (a potent intralesional corticosteroid); 4. ACCS intralesional injection alone; 5. Saline sham injections to the normal untreated ear. The endpoints for the study were ear thickness and ear weight at the end of the experiment. The thicker the ear and the more it weighs correlates with the degree of inflammation.

Results: Intralesional injection of ACCS was effective at reducing the inflammation induced by TPA at all time points beginning on day 2 of daily injections. Intralesional kenalog (10 mg/ml) injections induced a hematoma at the site of injection, which led to some inflammation and that is why there is not a substantial difference in ear thickness when comparing TPA+kenalog with TPA+control.

Conclusions: Intralesional ACCS did reduce skin inflammation but the topically applied ACCS in Example 1 above had a more potent effect. There was no difference in ear weight using either ACCS or intralesional kenalog compared with TPA+control.

Example 13

Wound Healing Model—Effects of ACCS in an Animal Model of Chronic Wound Healing

An art-accepted animal model for chronic granulating wound was used to study the effects of ACCS on chronic wound healing (Hayward P G, Robson M C: Animal models of wound contraction. In Barbul A, et al: Clinical and Experimental Approaches to Dermal and Epidermal Repair: Normal and Chronic Wounds. John Wiley & Sons, New York, 1990.).

Results: ACCS was effective in not allowing proliferation of tissue bacterial bioburden. ACCS allowed accelerated healing of the granulating wound significantly faster than the non-treated infected control groups.

Example 14

Arthroplasty Animal Model

An art accepted animal model for arthroplasty (see, for example, Bernthal, N. M., et al., PloS ONE, September 2010, Vol. 5, Issue 9, e12582) is used to evaluate the ACCS coated improved medical device of the invention and its ability to prevent and/or down-regulate the inflammatory response associated with implanted, inserted or transcutaneously placed medical devices. This model is also used to evaluate the ACCS coated improved medical device's ability to deliver, in a controlled manner, physiologically relevant inflammatory response-modulating cytokines and growth factors that are capable of preventing and/or down-regulating the inflammatory response associated with implanted, inserted or transcutaneously placed medical devices. This model is also used to evaluate the ACCS coated improved medical device's ability to deliver, in a controlled manner, physiologically relevant wound healing growth factors and cytokines that are capable of promoting healing of tissue at the medical device implantation, insertion or transcutaneous placement site in a patient.

The present invention may be embodied in other specific forms without departing from the spirit or essential attributes thereof. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

Throughout the specification various publications have been referred to. It is intended that each publication be incorporated by reference in its entirety into this specification.

What is claimed is:

1. An improved implantable medical device useful for surgical implantation into a subject's body, wherein the improvement to the implantable medical device comprises an implantable medical device having a coating on its surface, wherein the coating comprises Amnion-derived Cellular Cytokine Solution (ACCS) dispersed in a polymeric coating material, wherein the ACCS comprises about 5.0-16 ng/mL VEGF, about 3.5-4.5 ng/mL Angiogenin, about 100-165 pg/mL PDGF, about 2.5-2.7 ng/mL TGFβ2, about 0.68 µg/mL TIMP-1 and about 1.04 µg/mL TIMP-2.

2. The improved implantable medical device of claim 1 wherein the ACCS is lyophilized prior to dispersal in the polymeric coating material.

3. The improved implantable medical device of claim 1 which is selected from the group consisting of stents, joint replacement devices, tooth replacement devices, bone screws, bone repair rods, bone repair plates, bone repair wires, bone repair pins, spine screws, spine rods, artificial intervertebral discs, pacemakers, implantable defibrillators, cochlear implants and dental implants.

4. An improved insertable medical device useful for surgical insertion into a subject's body, wherein the improvement to the insertable medical device comprises an insertable medical device having a coating on its surface, wherein the coating comprises Amnion-derived Cellular Cytokine Solution (ACCS) dispersed in a polymeric coating material, wherein the ACCS comprises about 5.0-16 ng/mL VEGF, about 3.5-4.5 ng/mL Angiogenin, about 100-165 pg/mL PDGF, about 2.5-2.7 ng/mL TGFβ2, about 0.68 µg/mL TIMP-1 and about 1.04 µg/mL TIMP-2.

5. The improved insertable medical device of claim 4 wherein the ACCS is lyophilized prior to dispersal in the polymeric coating material.

6. The improved insertable medical device of claim 4 which is selected from the group consisting of stents, joint replacement devices, tooth replacement devices, bone screws, bone repair rods, bone repair plates, bone repair wires, bone repair pins, spine screws, spine rods, artificial intervertebral discs, pacemakers, implantable defibrillators, cochlear implants and dental implants.

7. An improved transcutaneous medical device useful for insertion into a subject's body, wherein the improvement to the transcutaneous medical device comprises a transcutaneous medical device having a coating on its surface, wherein the coating comprises Amnion-derived Cellular Cytokine Solution (ACCS) dispersed in a polymeric coating material, wherein the ACCS comprises about 5.0-16 ng/mL VEGF, about 3.5-4.5 ng/mL Angiogenin, about 100-165 pg/mL PDGF, about 2.5-2.7 ng/mL TGFβ2, about 0.68 µg/mL TIMP-1 and about 1.04 µg/mL TIMP-2.

8. The improved transcutaneous medical device of claim 7 wherein ACCS is lyophilized prior to dispersal in the polymeric coating material.

9. The improved transcutaneous medical device of claim 7 which is selected from the group consisting of stents, joint replacement devices, tooth replacement devices, bone screws, bone repair rods, bone repair plates, bone repair wires, bone repair pins, spine screws, spine rods, artificial intervertebral discs, pacemakers, implantable defibrillators, cochlear implants and dental implants.

10. A method for down-regulating the inflammatory response that occurs following the implantation, insertion or transcutaneous placement of a medical device in a patient, the method comprising the step of coating the medical device with ACCS dispersed in a polymeric coating material, wherein the ACCS comprises about 5.0-16 ng/mL VEGF, about 3.5-4.5 ng/mL Angiogenin, about 100-165 pg/mL PDGF, about 2.5-2.7 ng/mL TGFβ2, about 0.68 μg/mL TIMP-1 and about 1.04 μg/mL TIMP-2.

11. The method of claim 10 wherein the ACCS, is lyophilized prior to dispersal in the polymeric coating material.

12. The method of claim 10 wherein the medical device is selected from the group consisting of stents, joint replacement devices, tooth replacement devices, bone screws, bone repair rods, bone repair plates, bone repair wires, bone repair pins, spine screws, spine rods, artificial intervertebral discs, pacemakers, implantable defibrillators, cochlear implants and dental implants.

* * * * *